(12) United States Patent
Ohno

(10) Patent No.: US 11,389,050 B2
(45) Date of Patent: Jul. 19, 2022

(54) MEDICAL IMAGING APPARATUS INCLUDING TRANSMISSIVE SEAL FOR AN OPERATING DEVICE AND LIGHT FOR ILLUMINATING THE OPERATING DEVICE

(71) Applicant: Sony Olympus Medical Solutions Inc., Tokyo (JP)

(72) Inventor: Atsuomi Ohno, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 296 days.

(21) Appl. No.: 16/699,125

(22) Filed: Nov. 29, 2019

(65) Prior Publication Data

US 2020/0253459 A1  Aug. 13, 2020

(30) Foreign Application Priority Data

Feb. 8, 2019  (JP) .............................. JP2019-021468

(51) Int. Cl.
| | |
|---|---|
| *A61B 1/00* | (2006.01) |
| *A61B 1/04* | (2006.01) |
| *A61B 1/06* | (2006.01) |
| *A61B 1/05* | (2006.01) |
| *A61J 1/18* | (2006.01) |

(52) U.S. Cl.
CPC ............ *A61B 1/0008* (2013.01); *A61B 1/042* (2013.01); *A61B 1/05* (2013.01); *A61B 1/0676* (2013.01); *A61J 1/18* (2013.01); *A61B 1/00039* (2013.01)

(58) Field of Classification Search
USPC ........................................... 362/23.11, 23.05
See application file for complete search history.

(56) References Cited

U.S. PATENT DOCUMENTS

| | | | | |
|---|---|---|---|---|
| 7,608,039 | B1* | 10/2009 | Todd .................. | A61B 1/00039 200/310 |
| 10,347,443 | B1* | 7/2019 | Wu ...................... | G02B 6/0023 |
| 2008/0130263 | A1* | 6/2008 | Liu ...................... | G02B 6/0055 362/23.05 |
| 2008/0312649 | A1* | 12/2008 | Guerra ............... | A61B 18/1445 606/41 |
| 2013/0223042 | A1* | 8/2013 | Kim ..................... | H01H 23/025 362/23.04 |

FOREIGN PATENT DOCUMENTS

JP         2018-153472 A       10/2018

* cited by examiner

*Primary Examiner* — John P Leubecker
(74) *Attorney, Agent, or Firm* — Xsensus LLP

(57) ABSTRACT

A medical imaging apparatus includes: a casing connected to an insertion portion inserted into a subject and the casing configured to capture a subject image from the subject, the casing being gripped by a user; an operating device provided on an outer surface of the casing and including a button configured to receive a user's operation; a transmissive member having translucency and configured to seal the casing by being provided in the casing; a light emitting element provided in an internal space of the casing sealed by the transmissive member and configured to emit light for illuminating the operating device via the transmissive member; an image sensor configured to capture the subject image; and a lens unit configured to form the subject image on the image sensor.

9 Claims, 5 Drawing Sheets

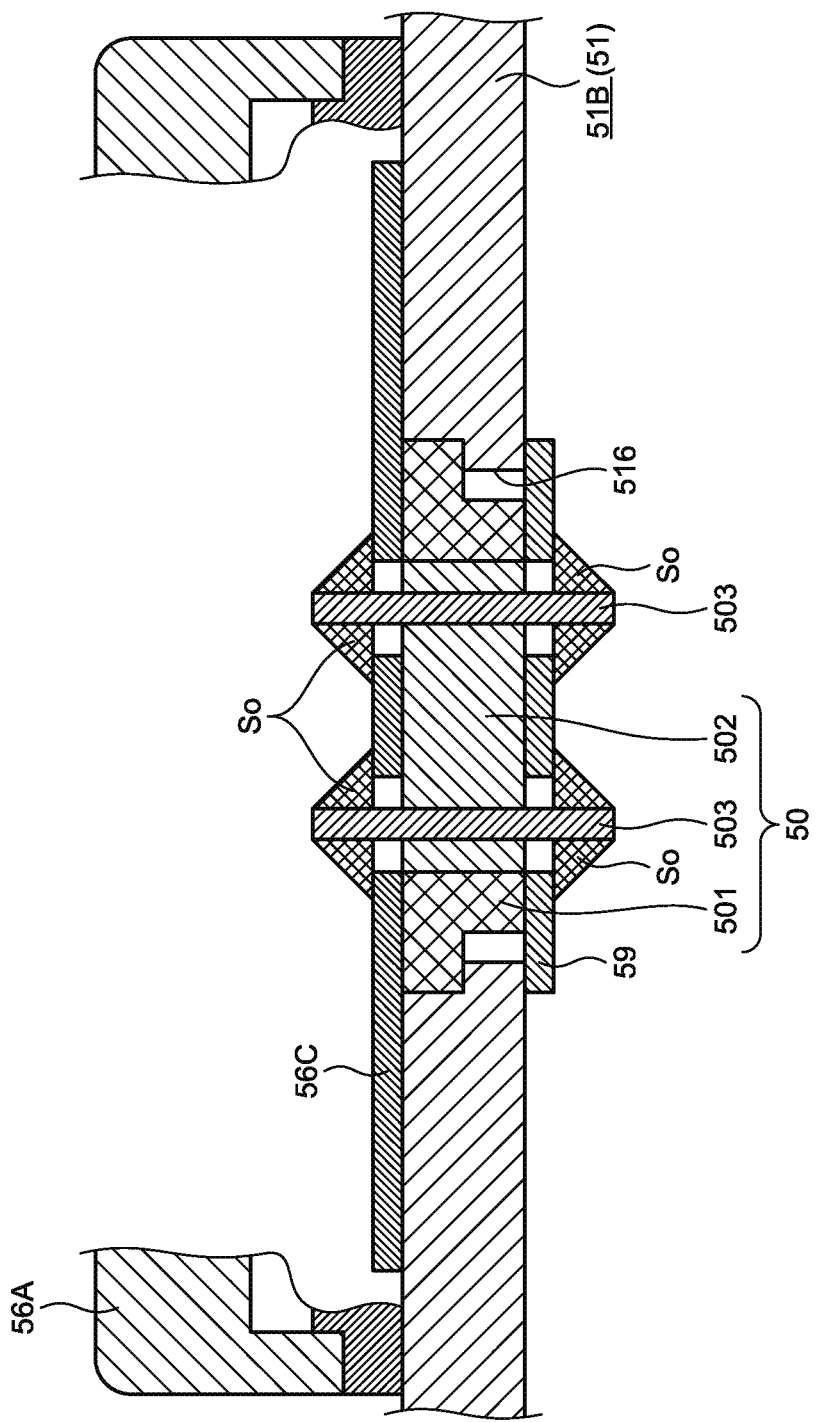

MEDICAL IMAGING APPARATUS INCLUDING TRANSMISSIVE SEAL FOR AN OPERATING DEVICE AND LIGHT FOR ILLUMINATING THE OPERATING DEVICE

This application claims priority from Japanese Application No. 2019-021468, filed on Feb. 8, 2019, the contents of which are incorporated by reference herein in its entirety.

BACKGROUND

The present disclosure relates to a medical imaging apparatus.

There is a known medical observation system that images an inside of a subject (living body) such as a human using an image sensor and observes the inside of the living body (refer to JP 2018-153472 A, for example).

The medical observation system (medical endoscope system) described in JP 2018-153472 A includes: an insertion portion (rigid endoscope) configured to be inserted into a subject to capture a subject image, that is, an image of the subject; and a medical imaging apparatus (endoscope camera head) to which the insertion portion is detachably connected and that includes an image sensor that images the subject image captured by the insertion portion.

Here, the medical imaging apparatus includes: a casing that stores an image sensor or the like; and an operating unit that is provided on an outer surface of the casing and that has a button that receives user's operation.

SUMMARY

Meanwhile, the medical imaging apparatus may be used in a dim environment. That is, the visibility of buttons provided on an operating unit of the medical imaging apparatus is reduced when the medical imaging apparatus is used. This leads to a problem that it is difficult to judge which is a correct button for executing a desired function when a user such as a doctor presses a button for executing a desired function, among buttons provided on the operating unit of the medical imaging apparatus.

According to one aspect of the present disclosure, there is provided a medical imaging apparatus includes: a casing connected to an insertion portion inserted into a subject and the casing configured to capture a subject image from the subject, the casing being gripped by a user; an operating device provided on an outer surface of the casing and including a button configured to receive a user's operation; a transmissive member having translucency and configured to seal the casing by being provided in the casing; a light emitting element provided in an internal space of the casing sealed by the transmissive member and configured to emit light for illuminating the operating device via the transmissive member; an image sensor configured to capture the subject image; and a lens unit configured to form the subject image on the image sensor.

BRIEF DESCRIPTION OF THE DRAWINGS

FIG. 5 is a cross-sectional view illustrating a connection structure between an operation substrate and an internal substrate.

DETAILED DESCRIPTION

Figure 1:
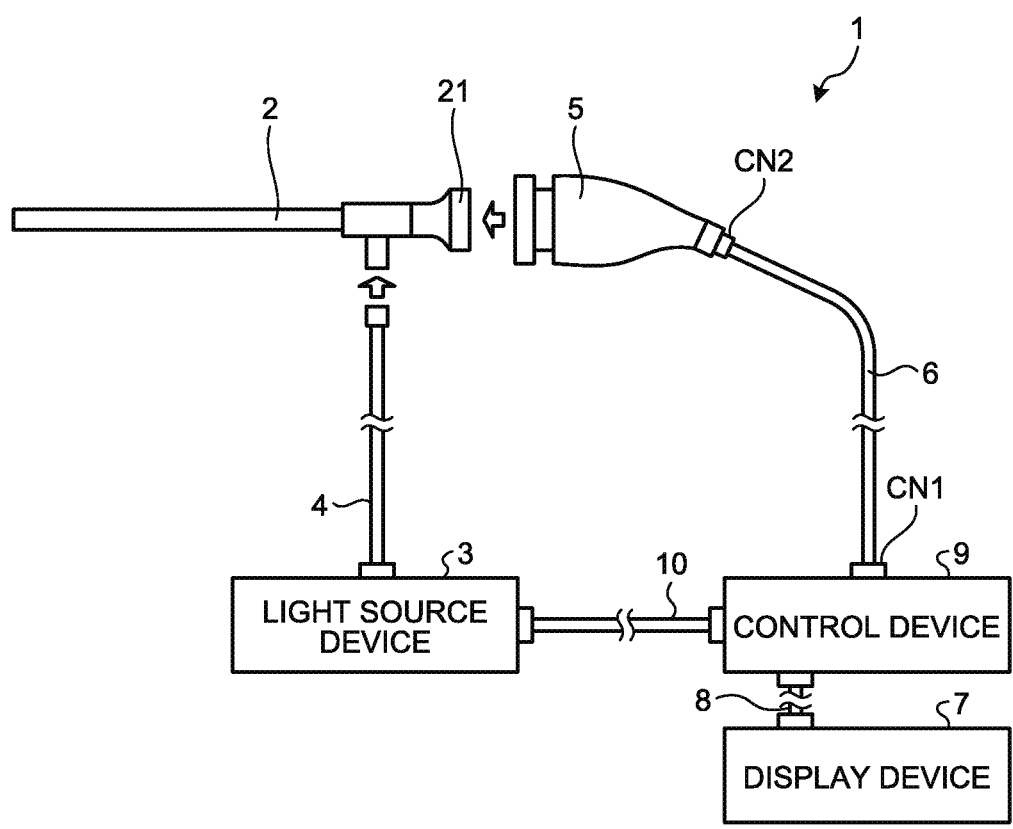
FIG. 1 is a view illustrating a schematic configuration of a medical observation system according to an embodiment.

Hereinafter, embodiments for carrying out the present disclosure (hereinafter referred to as embodiments) will be described with reference to the drawings. The present disclosure is not limited to the embodiments described below. In the description of the drawings, the identical reference numerals will be used to denote identical portions.

Schematic Configuration of Medical Observation System

FIG. 1 is a view illustrating a schematic configuration of a medical observation system 1 according to the present embodiment.

The medical observation system 1 is a system that is used in the medical field and observes the inside of a subject (living body). As illustrated in FIG. 1, the medical observation system 1 includes an insertion portion 2, a light source device 3, a light guide 4, an endoscope camera head 5, a first transmission cable 6, a display device 7, a second transmission cable 8, a control device 9, and a third transmission cable 10.

In the present embodiment, the insertion portion 2 is implemented by a rigid endoscope. That is, the insertion portion 2 has an elongated shape that is entirely rigid, or partially rigid with a partially flexible portion, so as to be inserted into a living body. The insertion portion 2 includes an optical system having one or more lenses and configured to collect light (subject image) from the living body.

The light source device 3 is connected to one end of the light guide 4, and supplies light for illuminating the inside of the living body to the one end of the light guide 4 under the control of the control device 9.

In the present embodiment, the light source device 3 is separated from the control device 9. However, the configuration is not limited to this, and it is allowable to employ a configuration in which the light source device 3 is provided inside the control device 9.

The light guide 4 has one end detachably connected to the light source device 3 and the other end detachably connected to the insertion portion 2. The light guide 4 transmits the light supplied from the light source device 3 from one end to the other end and supplies the light to the insertion portion 2. The light supplied to the insertion portion 2 is emitted from a distal end of the insertion portion 2 and applied to the inside of the living body. The light (subject image) applied to the inside of the living body is collected by the optical system in the insertion portion 2.

The endoscope camera head 5 corresponds to the medical imaging apparatus according to the present disclosure. The endoscope camera head 5 is detachably connected to a proximal end (an eyepiece 21 (FIG. 1)) of the insertion portion 2. The endoscope camera head 5 captures the subject image collected by the insertion portion 2 under the control of the control device 9, and outputs an image signal (RAW signal) obtained by the imaging. The image signal is an image signal of 4K resolution or more.

A detailed configuration of the endoscope camera head 5 will be described below.

The first transmission cable 6 has one end detachably connected to the control device 9 via a connector CN1 (FIG. 1), and has the other end detachably connected to the endoscope camera head 5 via a connector CN2 (FIG. 1). The first transmission cable 6 transmits the image signal output from the endoscope camera head 5 to the control device 9, and transmits each of the control signal, synchronization signal, clock, power, or the like output from the control device 9 to the endoscope camera head 5.

Note that the image signal or the like transmitted from the endoscope camera head 5 to the control device 9 via the first transmission cable 6 may be transmitted in an optical signal or in an electrical signal. The similar applies to transmission of control signals, synchronization signals, and clocks from the control device 9 to the endoscope camera head 5 via the first transmission cable 6.

The display device 7 is implemented by a display using liquid crystal, organic Electro Luminescence (EL), or the like, and displays an observation image based on a video signal from the control device 9 under the control of the control device 9.

The second transmission cable 8 has one end detachably connected to the display device 7 and the other end detachably connected to the control device 9. The second transmission cable 8 transmits the video signal processed by the control device 9 to the display device 7.

The control device 9 includes a central processing unit (CPU), or the like, and comprehensively controls operation of the light source device 3, the endoscope camera head 5, and the display device 7.

Specifically, the control device 9 performs various types of processing on the image signal acquired from the endoscope camera head 5 via the first transmission cable 6, thereby generating a video signal, and then outputs the video signal to the display device 7 via the second transmission cable 8. The display device 7 then displays an image based on the video signal. The control device 9 outputs a control signal or the like to the endoscope camera head 5 and the light source device 3 via the first and third transmission cables 6 and 10.

The third transmission cable 10 has one end detachably connected to the light source device 3 and the other end detachably connected to the control device 9. The third transmission cable 10 transmits a control signal from the control device 9 to the light source device 3.

Configuration of endoscope camera head Next, a configuration of the endoscope camera head 5 will be described.

Figure 2:
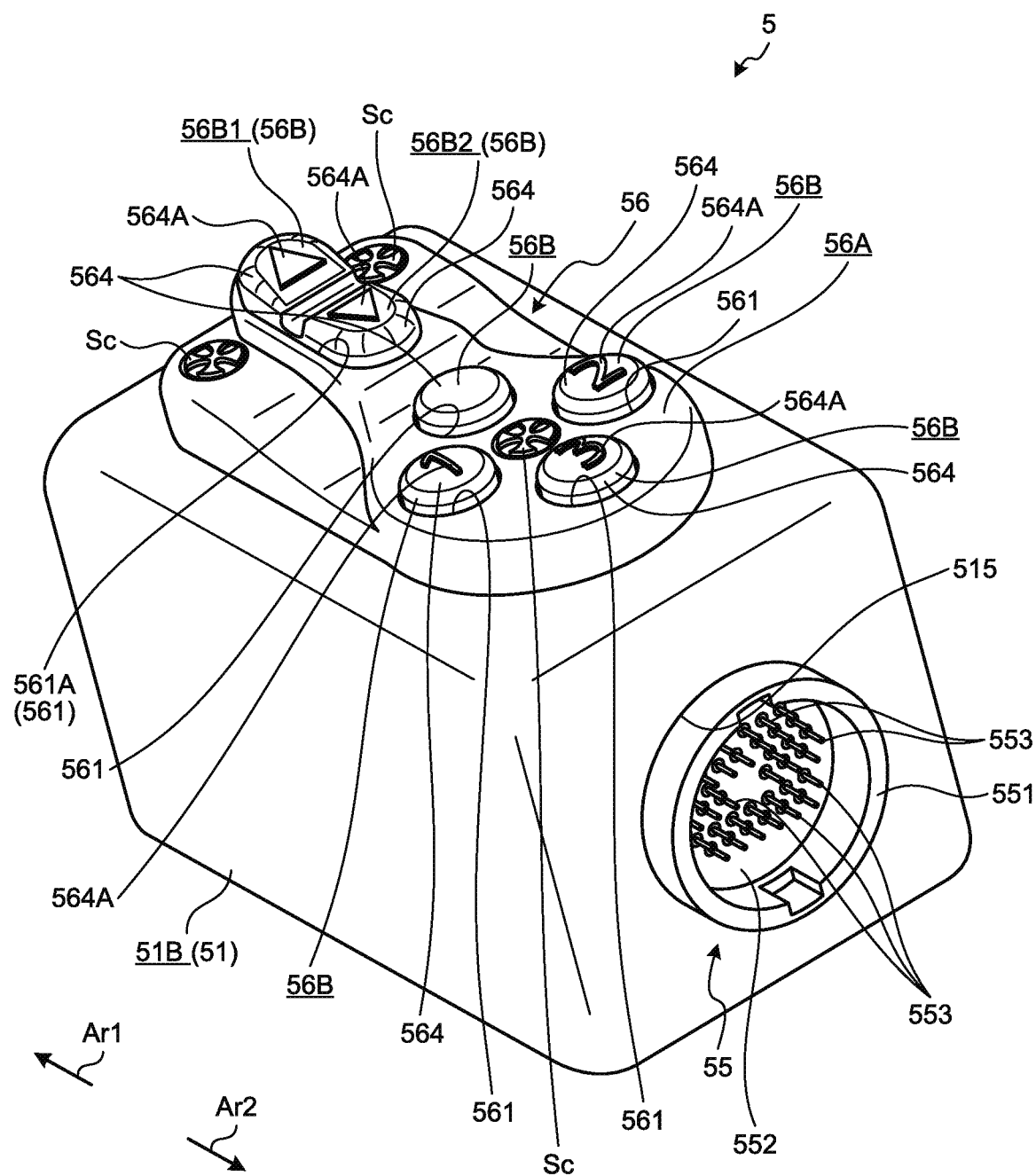
FIG. 2 is a view illustrating an endoscope camera head.
Figure 3:
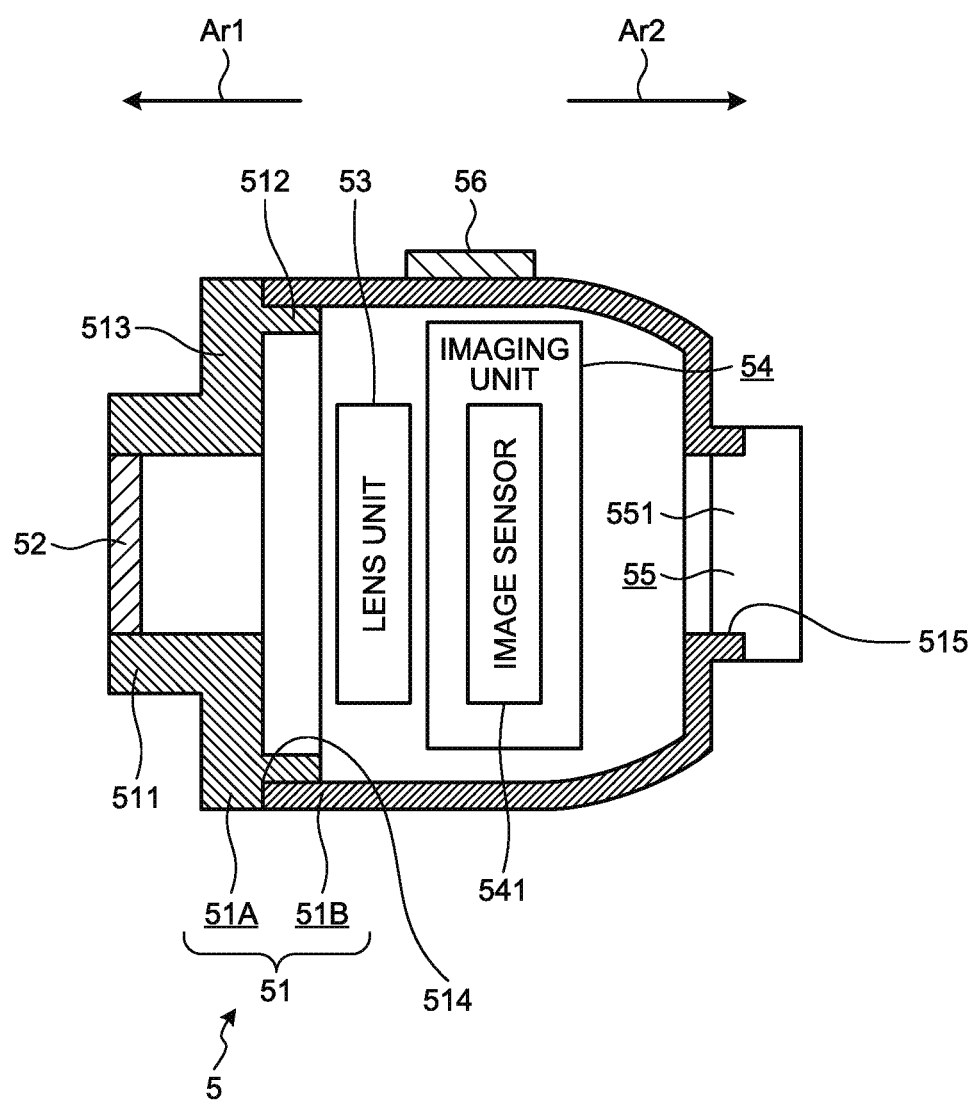
FIG. 3 is a view illustrating an endoscope camera head.

FIGS. 2 and 3 are views illustrating the endoscope camera head 5. Specifically, FIG. 2 is a perspective view illustrating an appearance of the endoscope camera head 5. FIG. 3 is a cross-sectional view illustrating an internal configuration of the endoscope camera head 5.

In FIGS. 2 and 3, for convenience of explanation, the side to which the proximal end (eyepiece 21) of the insertion portion 2 is connected is referred to as a distal end side Ar1, and the side to which the first transmission cable 6 is connected is referred to as a proximal end side Ar2. Note that FIG. 3 omits illustration of a transmissive member 57 and a light emitting element 58 for convenience of explanation.

Figure 4:
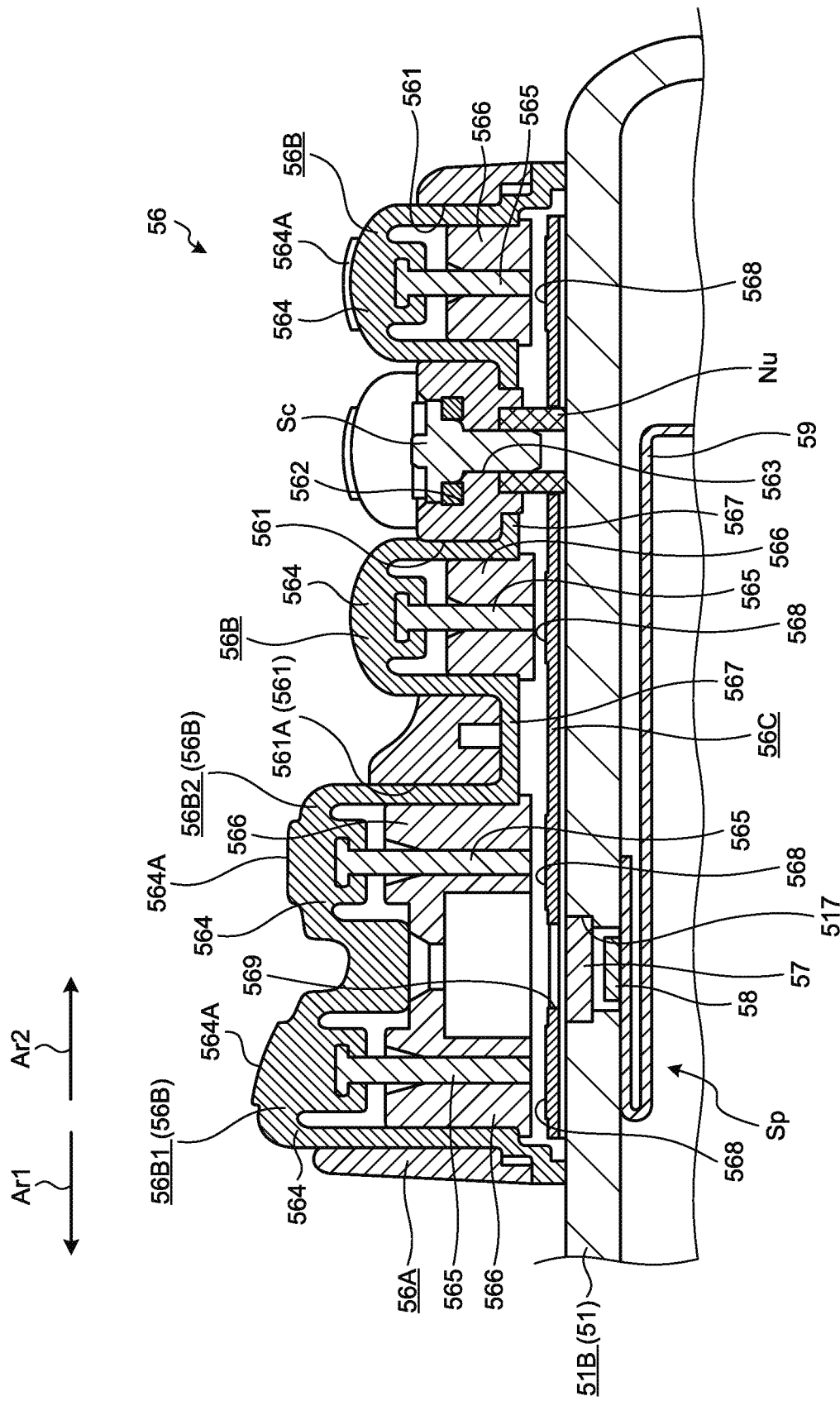
FIG. 4 is a cross-sectional view illustrating configurations of an operating unit, a transmissive member, and a light emitting element.

As illustrated in FIG. 2 or 3, the endoscope camera head 5 includes a casing 51, an optical element 52 (FIG. 3), a lens unit 53 (FIG. 3), and an imaging unit 54 (FIG. 3), a first hermetic connector 55, an operating unit 56, a transmissive member 57 (refer to FIG. 4), and a light emitting element 58 (refer to FIG. 4).

The casing 51 is a portion to which the insertion portion 2 is connected and that is held by a user such as a doctor. In the present embodiment, the casing 51 includes two members, a front casing 51A and a rear casing 51B, as illustrated in FIG. 3.

The front casing 51A is a member that holds the optical element 52 and secures the optical element 52 to the rear casing 51B, and is formed of aluminum, aluminum alloy, stainless steel, titanium, titanium alloy, or the like. As illustrated in FIG. 3, the front casing 51A includes first and second tube portions 511 and 512 and a connecting portion 513.

The first tube portion 511 is formed in a tube shape (for example, a cylindrical shape), and is positioned closer to the distal end side Ar1 than from the second tube portion 512 and the connecting portion 513. The first tube portion 511 holds the optical element 52 on the inner peripheral surface.

The second tube portion 512 is formed in a tube shape (for example, a cylindrical shape) having an inner diameter size larger than the outer shape size of the first tube portion 511.

The connecting portion 513 is formed in a circular shape (for example, an annular shape) and connects the first and second tube portions 511 and 512 to each other.

The first and second tube portions 511 and 512 and the connecting portion 513 are integrally formed so that their center axes are aligned with each other.

The rear casing 51B is formed of aluminum, aluminum alloy, stainless steel, titanium, titanium alloy, or the like. As illustrated in FIG. 3, the rear casing 51B is formed in a tube shape having a distal end side aperture 514 and a proximal end-side aperture 515 at the end of the distal end side Ar1 and the end of the proximal end side Ar2, respectively. More specifically, the rear casing 51B extends from the end of the distal end side Ar1 toward the proximal end side Ar2 with substantially the same inner shape size, and has its inner shape size reduced at the end portion of the proximal end side Ar2.

The front casing 51A and the rear casing 51B are secured to each other by welding in a state where the second tube portion 512 is fitted in the distal end side aperture 514. That is, the gap between the front casing 51A and the rear casing 51B is hermetically sealed.

The optical element 52 is secured to the inside of the first tube portion 511 by brazing, for example, and hermetically seals the aperture of the distal end side Art of the casing 51. The optical element 52 is formed of flat sapphire glass, for example.

The lens unit 53 forms a subject image collected by the insertion portion 2 and that has passed through the optical element 52, on an imaging surface of the imaging unit 54 (image sensor 541).

The imaging unit 54 images the inside of the living body under the control of the control device 9. The imaging unit 54 includes: an image sensor 541 such as a Charge Coupled Device (CCD) or Complementary Metal Oxide Semiconductor (CMOS) that receives a subject image collected by the insertion portion 2 and imaged by the lens unit 53 via the optical element 52 and converts the image into an electrical signal; and a signal processing unit (not illustrated) that performs signal processing (A/D conversion, etc.) on the electrical signal (analog signal) from the image sensor 541 and outputs an image signal (RAW signal (digital signal)).

As illustrated in FIG. 2, the first hermetic connector 55 includes: a tube shaped (e.g., cylindrical) outer shell 551, a plate body 552 that closes the inside of the outer shell 551; and a plurality of conductive pins 553 that penetrates the front and back of the plate body 552 so as to be attached to the plate body 552 while being insulated from each other, and that is configured to be electrically connected to the imaging unit 54. Here, the outer shell 551 is formed of aluminum, aluminum alloy, stainless steel, titanium, titanium alloy, or the like. In the first hermetic connector 55, the outer shell 551 is secured to the inner surface of the proximal end-side aperture 515 by welding so as to hermetically seal the proximal end-side aperture 515.

The connector CN2 is detachably connected to the first hermetic connector 55 described above.

Here, the connector CN2 includes a tube shaped (e.g., cylindrical) outer shell (not illustrated), an insulator (not illustrated) that closes the inside of the outer shell, and a plurality of contacts (not illustrated) provided on the insulator. The plurality of conductive pins 553 of the first hermetic connector 55 is each inserted to each of the plurality of contacts when the connector CN2 is attached to the first hermetic connector 55, causing the plurality of contacts to be electrically connected to the plurality of conductive pins 553 and to be electrically connected to the first transmission cable 6.

That is, the image signal (RAW signal (digital signal)) output from the imaging unit 54 is output to the first transmission cable 6 via the first hermetic connector 55 and the connector CN2. In addition, the control signal output from the control device 9 is output to the electronic components (including the imaging unit 54) in the casing 51 via the first transmission cable 6, the connector CN2, and the first hermetic connector 55.

FIG. 4 is a cross-sectional view illustrating a configuration of the operating unit 56, the transmissive member 57, and the light emitting element 58.

As illustrated in FIG. 4, the operating unit 56 is attached to the outer surface of the rear casing 51B using a nut Nu secured by welding onto the outer surface of the rear casing 51B and using a screw Sc fastened to the nut Nu. In addition, the operating unit 56 receives operation by a user such as a doctor. As illustrated in FIG. 4, the operating unit 56 includes a button frame 56A, a plurality of buttons 56B, and an operation substrate 56C.

The button frame 56A is formed in a container shape having an aperture on the lower side of FIG. 4. A plurality of apertures 561 penetrating each of the inside and outside of the button frame 56A is formed on the bottom surface (the upper surface in FIG. 4) of the button frame 56A. In addition, a recess 562 that is recessed downward in FIG. 4 is formed on the bottom surface of the button frame 56A. Furthermore, an insertion hole 563 through which the screw Sc is inserted is formed at the bottom of the recess 562. The screw Sc is fastened to the nut Nu via the insertion hole 563, whereby the button frame 56A is attached to the outer surface of the rear casing 51B with the screw Sc.

The plurality of buttons 56B is a portion that receives operation by a user such as a doctor (pressed by the user). As illustrated in FIG. 4, the button 56B includes a button body 564, a pin 565, and a guide member 566.

The button body 564 is formed of an elastic member having translucency, and is formed in a container shape with an aperture on the lower side in FIG. 4, and is disposed in a state of being exposed to the outside of the button frame 56A via the aperture 561. In the present embodiment, each of button bodies 564 constituting each of the plurality of buttons 56B is connected, on a container shaped aperture side on the button body 564, to each other by a plate-like base 567 (FIG. 4) formed of the same material as the button body 564. Furthermore, an outer front surface of the button body 564 exposed to the outside of the button frame 56A via the aperture 561 includes a character 564A (FIGS. 2 and 4) for identifying a function to be executed when the button body 564 is pressed. In the present embodiment, the character 564A is provided in the form of protrusion on a part of the outer front surface of the button body 564 by molding. However, the present disclosure is not limited to this, and the character 564A may be provided in the form of recess on a part of the outer front surface of the button body 564 by molding.

In the button body 564, the pin 565 is disposed with one end secured to the bottom of the button body 564 and in a state extending from the one end to the lower side of FIG. 4. In a case where the button body 564 is deformed by being pressed by a user such as a doctor, the pin 565 moves downward in FIG. 4 until the operation substrate 56C (switch element 568) is pressed together with the deformation. When the button body 564 returns to the original state, the pin 565 is separated from the operation substrate 56C.

Similarly to the button body 564, the guide member 566 is formed of an elastic member having translucency. The guide member 566 has a cylindrical shape through which the pin 565 is inserted, and is press-fitted into the button body 564. In addition, the guide member 566 guides the up-down movement of the pin 565 in FIG. 4 according to the operation of the button body 564 by a user such as a doctor.

In the present embodiment, a pair of buttons 56B1 and 56B2, among the plurality of buttons 56B, is formed integrally with each other as illustrated in FIG. 2 or 4, and is disposed in one aperture 561A out of the plurality of apertures 561 in the button frame 56A. More specifically, in the pair of buttons 56B1 and 56B2, each of the button bodies 564 is integrally formed, each guide member 566 is integrally formed, and each of pins 565 is provided independently.

As illustrated in FIG. 4, the operation substrate 56C is attached to the outer surface of the rear casing 51B and covered with the button frame 56A. That is, the operation substrate 56C is provided between the outer surface of the rear casing 51B and the plurality of buttons 56B. A plurality of switch elements 568 is mounted on the operation substrate 56C, corresponding to the plurality of buttons 56B. The operation substrate 56C (switch element 568) outputs an operation signal corresponding to the operation of the button 56B by a user such as a doctor to an internal substrate 59 disposed in the rear casing 51B.

Here, the internal substrate 59 is electrically connected to the control device 9 via the first hermetic connector 55, the connector CN2, and the first transmission cable 6. That is, an operation signal from the operation substrate 56C (switch element 568) is output to the control device 9 via the internal substrate 59, the first hermetic connector 55, the connector CN2, and the first transmission cable 6.

FIG. 5 is a cross-sectional view illustrating a connection structure between the operation substrate 56C and the internal substrate 59.

The operation substrate 56C and the internal substrate 59 are electrically connected to each other via a second hermetic connector 50 as illustrated in FIG. 5.

Here, as illustrated in FIG. 5, the second hermetic connector 50 includes a tube shaped (e.g., cylindrical) outer shell 501, an insulating plate body 502 that is formed of glass or the like and closes the inside of the outer shell 501, and a plurality of (two in the example of FIG. 5) conductive pins 503 penetrating the front and back of the plate body 502. The second hermetic connector 50 is joined by welding between the inner surface of a through hole 516 formed in the rear casing 51B and the outer surface of the outer shell 501 in a state where the second hermetic connector 50 is fitted in the through hole 516, and thereby is secured to the rear casing 51B. That is, the through hole 516 is hermetically sealed with the second hermetic connector 50.

The operation substrate 56C is electrically connected to the plurality of conductive pins 503 with solder So. Similarly, the internal substrate 59 is electrically connected to the plurality of conductive pins 503 with solder So. That is, the operation substrate 56C and the internal substrate 59 are electrically connected to each other via the plurality of conductive pins 503.

Note that the number of conductive pins 503 is not limited to two, and may be one, or three or more.

The transmissive member 57 is formed of a member having translucency, such as sapphire glass, and is secured, by brazing, for example, into a through hole 517 (FIG. 4) formed in the rear casing 51B. That is, the through hole 517 is hermetically sealed with the transmissive member 57. Hereinafter, an internal space of the casing 51 sealed with the optical element 52, the first and second hermetic connectors 55 and 50, and the transmissive member 57 will be referred to as an internal space Sp (FIG. 4).

In the present embodiment, the transmissive member 57 (through hole 517) is provided at a position facing the position between the pair of buttons 56B1 and 56B2 in the operating unit 56, as illustrated in FIG. 4. That is, the transmissive member 57 (through hole 517) is covered with the operating unit 56.

The light emitting element 58 is implemented by a light emitting diode (LED) or the like, and is electrically connected to the internal substrate 59. The light emitting element 58 emits light in accordance with the power supplied via the internal substrate 59, under the control of the control device 9. That is, the internal substrate 59 serves as a power supply path to the light emitting element 58 and corresponds to a flexible printed circuit board according to the present disclosure.

In the present embodiment, the light emitting element 58 is provided in the through hole 517 in the internal space Sp as illustrated in FIG. 4. The light emitted from the light emitting element 58 is applied to the pair of buttons 56B1 and 56B2 via the transmissive member 57. The light applied to the pair of buttons 56B1 and 56B2 is transmitted from the back surface side (the lower side in FIG. 4) to the outer front surface side (the upper side in FIG. 4) of the pair of buttons 56B1 and 56B2.

Here, the operation substrate 56C includes a through hole 569 (FIG. 4) in a passage region (region facing the transmissive member 57) of light emitted from the light emitting element 58 and directed toward the buttons 56B1 and 56B2 via the transmissive member 57. That is, the operation substrate 56C is provided in a region other than the passage region.

Furthermore, as illustrated in FIG. 4, the internal substrate 59 covers the through hole 517 from the internal space Sp side. That is, the internal substrate 59 is located between the light emitting element 58 and the image sensor 541. The internal substrate 59 also has a function as a light shielding member that shields light from the light emitting element 58 toward the image sensor 541.

According to the present embodiment described above, the following effects may be obtained.

The endoscope camera head 5 according to the present embodiment includes the light emitting element 58 that emits light for illuminating the operating unit 56.

Therefore, it is possible to improve the visibility of the button 56B by the light emitted from the light emitting element 58. Therefore, it is possible to obtain a higher visibility of the button 56B even in a dim environment when the user such as a doctor presses the button 56B for executing a desired function among the plurality of buttons 56B provided on the operating unit 56. Accordingly, it is possible for the user such as a doctor to easily determine which button 56B is a button for executing the desired function.

Meanwhile, the endoscope camera head 5 is subjected to disinfection treatment using a disinfectant solution or autoclave treatment before observation into the living body. For this reason, it is necessary to protect the light emitting element 58 from the disinfectant solution or high-temperature and high-pressure steam in the autoclave treatment.

The endoscope camera head 5 according to the present embodiment includes the transmissive member 57 that has translucency and seals the casing 51 by being provided in the casing 51. The light emitting element 58 is provided in the internal space Sp of the casing 51 sealed with the transmissive member 57.

Therefore, it is possible to effectively protect the light emitting element 58 from the disinfectant solution or the high-temperature and high-pressure steam in the autoclave treatment while improving the visibility of the button 56B.

In the endoscope camera head 5 according to the present embodiment, the transmissive member 57 is covered with the operating unit 56. That is, the light emitted from the light emitting element 58 and passing through the transmissive member 57 is applied to the back surface side of the button 56B and is transmitted from the back surface side toward the outer front surface side.

For this reason, it is possible to generate the state in which the button 56B itself emits light in a pseudo manner, leading to satisfactory improvement of the visibility of the button 56B.

In the endoscope camera head 5 according to the present embodiment, the operation substrate 56C is provided in a region other than a region where the light emitted from the light emitting element 58 is transmitted toward the button 56B via the transmissive member 57, between the outer surface of the casing 51 and the button 56B.

Therefore, the amount of light directed toward the button 56B will not be reduced by the operation substrate 56C, leading to satisfactory improvement of the visibility of the button 56B.

In the endoscope camera head 5 according to the present embodiment, the transmissive member 57 is provided at a position facing the position between the pair of buttons 56B1 and 56B2 in the operating unit 56.

This configuration enables a structure of improving the visibility of the pair of buttons 56B1 and 56B2 by the single light emitting element 58, leading to reduction of the number of components.

In the endoscope camera head 5 according to the present embodiment, the light emitting element 58 is provided in the through hole 517 inside the internal space Sp. The internal substrate 59 is located between the light emitting element 58 and the image sensor 541 and shields light directed from the light emitting element 58 toward the image sensor 541.

For this reason, the light traveling from the light emitting element 58 toward the image sensor 541 is shielded by the inner surface of the through hole 517 and by the internal substrate 59. This makes it possible to suppress the influence of the light emitted from the light emitting element 58 on the observation image.

Furthermore, the number of components may be reduced as compared with a configuration in which the light shielding member is provided separately from the internal substrate 59.

Other Embodiments

While the above is description of the modes for carrying out the present disclosure, the present disclosure should not be limited by only the embodiments described above.

In the above-described embodiment, the endoscope camera head 5 is implemented as the medical imaging apparatus according to the present disclosure, but the present disclosure is not limited to this. For example, the present disclosure may use a configuration in which the insertion portion 2 is implemented by a flexible endoscope, and a configuration including an image sensor provided at the distal end of the flexible endoscope together with an endoscope camera head 5 that omits the lens unit 53 and the imaging unit 54 to be implemented as the medical imaging apparatus according to the present disclosure.

In the above-described embodiment, the transmissive member 57 (through hole 517) is covered with the operating unit 56. That is, the light emitted from the light emitting element 58 and passing through the transmissive member 57 is applied to the back surface side of the pair of buttons 56B1 and 56B2 and then is transmitted from the back surface side toward the outer front surface side. The present disclosure, however, is not limited to this.

For example, the transmissive member 57 (through hole 517) may be provided in a region other than a region covered by the operating unit 56. The light emitted from the light emitting element 58 and passing through the transmissive member 57 is applied onto the outer front surface of the operating unit 56 (side surface of the operating unit 56). In a case where such a configuration is employed, the button body 564 and the guide member 566 would not have to be formed of a material having translucency.

Moreover, the first and second tube portions 511 and 512 and the connecting portion 513 are not limited to the integral configuration in which their center axes are aligned with each other but their center axes may be not aligned.

According to the medical imaging apparatus of the present disclosure, it is possible to improve the visibility of the button.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A medical imaging apparatus comprising:
    a casing connected to an insertion portion configured to be inserted into a subject, the casing being configured to be gripped by a user;
    an operating device provided on an outer surface of the casing and including a button configured to receive a user's operation;
    a transmissive seal having translucency and configured to seal the casing by being provided in the casing;
    a light source provided in an internal space of the casing sealed by the transmissive seal and configured to emit light for illuminating the operating device via the transmissive seal; and
    an image sensor within the casing configured to capture an image of the subject.

2. The medical imaging apparatus according to claim 1, wherein the casing includes a through hole penetrating an inside and outside of the casing, and
    the transmissive seal is in the through hole.

3. The medical imaging apparatus according to claim 1, wherein the operating device is provided on the outer surface of the casing in a state of covering at least a part of the transmissive seal; and
    the button has translucency and is configured to transmit light emitted from the light source and passing through the transmissive seal from a back surface side toward an outer front surface side.

4. The medical imaging apparatus according to claim 3, wherein the operating device further includes an operation substrate provided between the outer surface of the casing and the button, and a switch mounted on the operation substrate and configured to detect the user's operation on the button; and
    the operation substrate is provided in a region other than a passage region of light emitted from the light source and directed to the button through the transmissive seal.

5. The medical imaging apparatus according to claim 3, wherein the button includes a plurality of buttons, and
    the transmissive seal is provided at a position facing a position between the plurality of buttons in the operating device.

6. The medical imaging apparatus according to claim 1, wherein the image sensor is provided in the internal space, and
    the medical imaging apparatus further comprises a light shield between the light source and the image sensor in the internal space and configured to shield light traveling from the light source toward the image sensor.

7. The medical imaging apparatus according to claim 6, further comprising
    a flexible printed circuit board electrically connected to the light source and serving as a power supply path to the light source,
    wherein the flexible printed circuit board is the light shield.

8. The medical imaging apparatus according to claim 1, wherein the casing includes a through hole penetrating an inside and outside of the casing,
    the transmissive seal is provided in the through hole, and
    the light source is in the through hole within the internal space.

9. The medical imaging apparatus according to claim 1, further comprising a lens configured to form the image of the subject on the image sensor.

* * * * *